United States Patent
Abe et al.

(10) Patent No.: US 12,337,337 B2
(45) Date of Patent: Jun. 24, 2025

(54) LIQUID EJECTION NOZZLE AND LIQUID EJECTION DEVICE

(71) Applicant: SEIKO EPSON CORPORATION, Tokyo (JP)

(72) Inventors: Tomoki Abe, Matsumoto (JP); Osamu Katsuda, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 331 days.

(21) Appl. No.: 17/657,102

(22) Filed: Mar. 29, 2022

(65) Prior Publication Data

US 2022/0314242 A1 Oct. 6, 2022

(30) Foreign Application Priority Data

Mar. 31, 2021 (JP) ................................. 2021-059711

(51) Int. Cl.
*B05B 1/14* (2006.01)
*B05B 7/04* (2006.01)

(52) U.S. Cl.
CPC .............. *B05B 1/14* (2013.01); *B05B 7/0416* (2013.01)

(58) Field of Classification Search
CPC ................................. B05B 1/14; B05B 7/0416
USPC ........ 239/320–322, 329–337, 491, 492, 496, 239/504, 505, 518
See application file for complete search history.

(56) References Cited

U.S. PATENT DOCUMENTS

| | | | | |
|---|---|---|---|---|
| 4,109,869 A | * | 8/1978 | Brockelsby | B05B 11/0005 239/491 |
| 4,735,362 A | * | 4/1988 | Trautwein | B05B 1/3426 239/493 |
| 4,767,060 A | * | 8/1988 | Shay | B05B 7/0056 239/417 |
| 5,397,060 A | * | 3/1995 | Maas | B05B 7/0062 239/432 |
| 7,419,548 B2 | * | 9/2008 | Jeong | G02F 1/1341 239/333 |
| 2007/0235564 A1 | | 10/2007 | Whittaker et al. | |
| 2016/0199566 A1 | | 7/2016 | Schug et al. | |
| 2018/0086066 A1 | | 3/2018 | Irokawa | |
| 2018/0126392 A1 | | 5/2018 | Moser et al. | |

FOREIGN PATENT DOCUMENTS

| | | |
|---|---|---|
| CN | 107878029 A | 4/2018 |
| JP | H0866644 A | 3/1996 |
| JP | 2003012055 A | 1/2003 |
| JP | 2006272189 A | 10/2006 |
| JP | 2007253394 A | 10/2007 |

(Continued)

OTHER PUBLICATIONS

Office Action for JP Patent Application No. JP2021059711, issued on Nov. 26, 2024, 10 pages.

*Primary Examiner* — Steven J Ganey
(74) *Attorney, Agent, or Firm* — CHIP LAW GROUP

(57) ABSTRACT

A liquid ejection nozzle that has a nozzle hole and ejects a liquid from the nozzle hole in a ejection direction toward a target subject includes a nozzle plate having the nozzle hole, and a pressing member having a through hole having a diameter larger than a diameter of the nozzle hole at a position corresponding to the nozzle hole in the ejection direction and configured to press the nozzle plate from a downstream side in the ejection direction.

17 Claims, 15 Drawing Sheets

(56) References Cited

FOREIGN PATENT DOCUMENTS

| | | | |
|---|---|---|---|
| JP | 2015188756 | A | 11/2015 |
| JP | 2016534833 | A | 11/2016 |
| JP | 2017170513 | A | 9/2017 |
| JP | 2018103173 | A | 7/2018 |

* cited by examiner

LIQUID EJECTION NOZZLE AND LIQUID EJECTION DEVICE

The present application is based on and claims priority from JP Application Serial Number 2021-059711, filed Mar. 31, 2021, the disclosure of which is hereby incorporated by reference herein in its entirety.

BACKGROUND

1. Technical Field

The present disclosure relates to a liquid ejection nozzle and a liquid ejection device.

2. Related Art

Conventionally, a liquid ejection nozzle that ejects a liquid from a nozzle hole toward a target subject is used. For example, JP-A-2018-103173 discloses a handpiece capable of ejecting a fluid jet from a nozzle element. The handpiece of JP-A-2018-103173 is an example of a liquid ejection nozzle in which a liquid is ejected from a nozzle hole toward a target subject, but as described above, there are various types of liquid ejection nozzles that eject a liquid from a nozzle hole toward a target subject.

As a liquid ejection nozzle that ejects a liquid from a nozzle hole toward a target subject, a configuration in which a nozzle hole is formed in the nozzle plate and the liquid is ejected from the nozzle hole of the nozzle plate toward the target subject can be used. With such a configuration, it is possible to easily produce a liquid ejection nozzle with high precision. However, in the liquid ejection nozzle having such a configuration, there is a risk that the nozzle plate may be deformed by a pressure applied to the nozzle plate when the liquid is ejected from the nozzle hole. Therefore, an object of the present disclosure is to suppress deformation of a nozzle plate due to a pressure applied to the nozzle plate when a liquid is ejected from a nozzle hole.

SUMMARY

A liquid ejection nozzle according to the present disclosure for solving the problem is a liquid ejection nozzle that has a nozzle hole and ejects a liquid from the nozzle hole in an ejection direction toward a target subject and includes a nozzle plate having the nozzle hole, and a pressing member having a through hole having a diameter larger than a diameter of the nozzle hole at a position corresponding to the nozzle hole in the ejection direction and configured to press the nozzle plate from a downstream side in the ejection direction.

DESCRIPTION OF EXEMPLARY EMBODIMENTS

Figure 1:
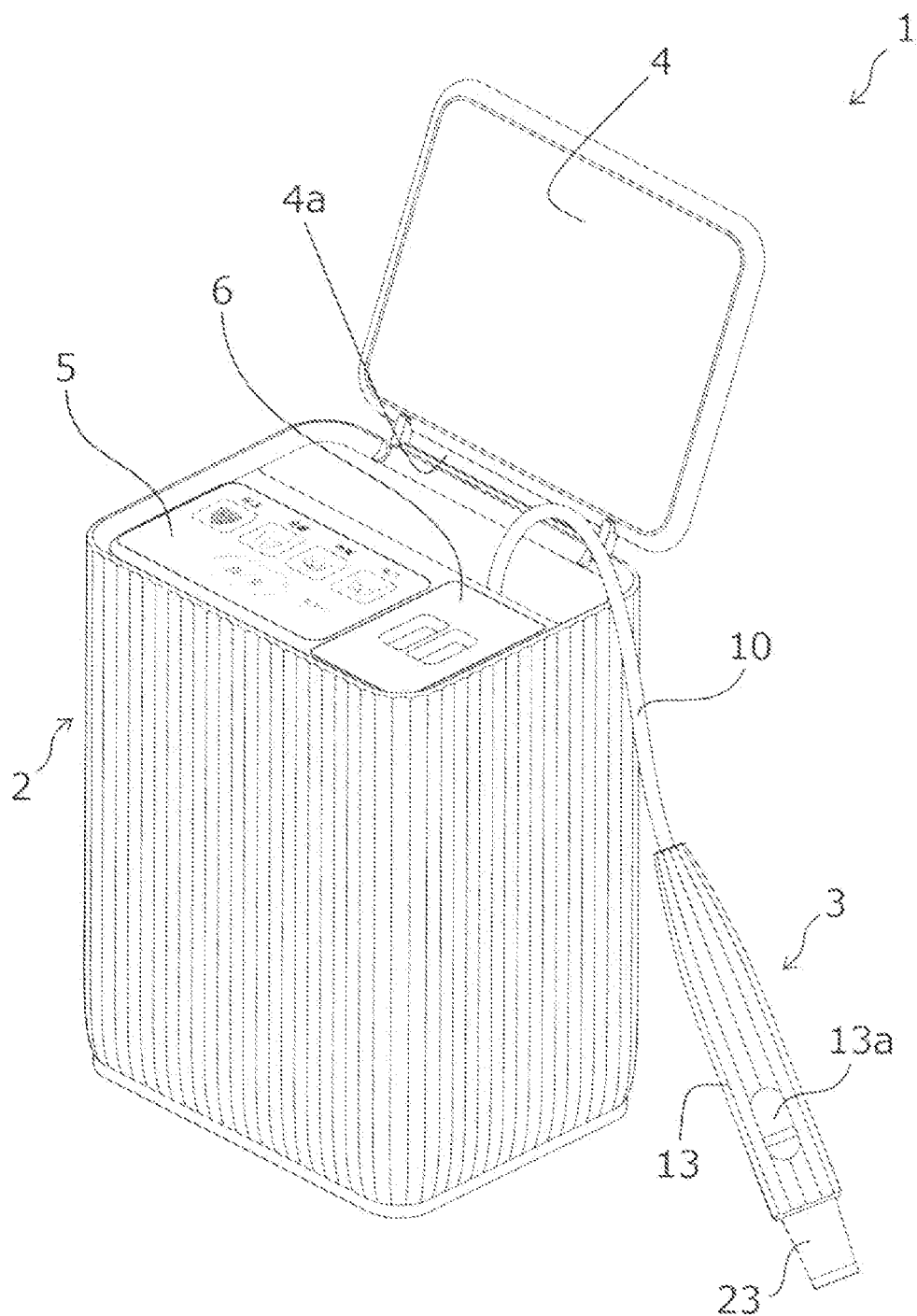
FIG. 1 is a schematic view of an entire liquid ejection device having a liquid ejection nozzle according to a first embodiment of the present disclosure.

First, the present disclosure will be schematically described.

A liquid ejection nozzle according to a first aspect of the present disclosure for solving the above problem is a liquid ejection nozzle that has a nozzle hole and ejects a liquid from the nozzle hole in an ejection direction toward a target subject, and includes a nozzle plate having the nozzle hole, and a pressing member having a through hole having a diameter larger than a diameter of the nozzle hole at a position corresponding to the nozzle hole in the ejection direction and configured to press the nozzle plate from the downstream side in the ejection direction.

According to the aspect, the pressing member having the through hole with the diameter larger than the diameter of the nozzle hole at the position corresponding to the nozzle hole in the ejection direction and configured to press the nozzle plate from the downstream side in the ejection direction is provided. Thus, due to the pressing member, deformation of the nozzle plate by a pressure applied to the nozzle plate can be suppressed without interfering with ejection of the liquid from the nozzle hole when the liquid is ejected from the nozzle hole.

In a liquid ejection nozzle according to the second aspect of the present disclosure, in the first aspect, a plurality of nozzle holes are provided in the nozzle plate.

According to the aspect, the plurality of nozzle holes are provided in the nozzle plate. As a result, the diameter of one nozzle hole can be reduced without reducing an amount of ejection of the liquid, and a sufficient amount of the liquid can be ejected at a high speed.

In a liquid ejection nozzle of a third aspect of the present disclosure, in the second aspect, one through hole is provided corresponding to each of the nozzle holes.

When the through hole is too large, an effect of suppressing the nozzle plate by the pressing member may decrease. However, according to the aspect, one through hole is provided corresponding to each nozzle hole. As a result, it is possible to suppress excessive enlargement of each of the through holes, and it is possible to suppress a decrease in the effect of suppressing the nozzle plate of the pressing member.

In a liquid ejection nozzle of a fourth aspect of the present disclosure, in the second aspect, one through hole is provided corresponding to the plurality of nozzle holes.

According to the aspect, one through hole is provided corresponding to the plurality of nozzle holes. As a result, the number of through holes can be reduced, and the pressing member having the through hole can be easily manufactured.

In a liquid ejection nozzle of a fifth aspect of the present disclosure, in any one of the first to fourth aspects, the pressing member is configured to be attached to and detached from the nozzle plate.

According to the aspect, the pressing member is configured to be attached to and detached from the nozzle plate. As a result, the pressing member can be easily replaced or cleaned.

In a liquid ejection nozzle of a sixth aspect of the disclosure, in any one of the first to fifth aspects, the pressing member includes a resin.

According to the aspect, the pressing member includes a resin. Because a shape made of the resin can be easily changed, the pressing member having the through hole can be easily manufactured using a resin.

In a liquid ejection nozzle of a seventh aspect of the present disclosure, in any one of the first to sixth aspects, in the pressing member, the through hole is subjected to a liquid-repellent treatment against a liquid.

According to the aspect, the through hole of the pressing member is subjected to the liquid repellent treatment against a liquid. As a result, when the liquid is ejected, it is possible to suppress wet-spreading of the liquid in the through hole and receiving of a force from the through hole and thus to suppress a reduction in ejection accuracy.

In a liquid ejection nozzle according to an eighth aspect of the present disclosure, in any one of the first to seventh aspects, the diameter of the through hole is equal to or less than a thickness of the pressing member in the ejection direction.

According to the aspect, the diameter of the through hole is equal to or less than the thickness of the pressing member in the ejection direction. As a result, it is possible to suppress excessive enlargement of the diameter of the through hole or excessive reduction in the thickness of the pressing member and thus to suppress a decrease in the effect of suppressing the nozzle plate of the pressing member.

A liquid ejection device of a ninth aspect of the present disclosure includes the liquid ejection nozzle according to any one of the first to eighth aspects, and a liquid supply device configured to supply the liquid to the liquid ejection nozzle.

According to this aspect, it is possible to suppress deformation of the nozzle plate due to a pressure applied to the nozzle plate without interfering with ejection of the liquid from the nozzle hole when the liquid is ejected from the nozzle hole.

In a liquid ejection device of a tenth aspect of the present disclosure, in the ninth aspect, the liquid supply device supplies the liquid to the liquid ejection nozzle using a gas pressure.

According to the aspect, the liquid can be easily supplied to the liquid ejection nozzle using a gas pressure.

First Embodiment

Hereinafter, embodiments according to the present disclosure will be described with reference to the accompanying drawings. Here, a liquid ejection device 1 is described as a liquid ejection device for facial skin or the like. Of course, the liquid ejection device 1 is not limited to that for facial skin, and can be applied to, for example, cleaning of skin such as that on the arms, hands, feet, and back, and can also be applied to cleaning of articles other than living bodies.

First, the outline of the liquid ejection device 1 of the embodiment will be described with reference to FIGS. 1 to 5. The liquid ejection device 1 of the embodiment cleans skin, such as that on a face, with a liquid ejected from a liquid ejection nozzle 3. Specifically, the liquid ejection device 1 of the embodiment includes a liquid ejection nozzle 3 that ejects a liquid, and a liquid supply device 2.

Figure 2:
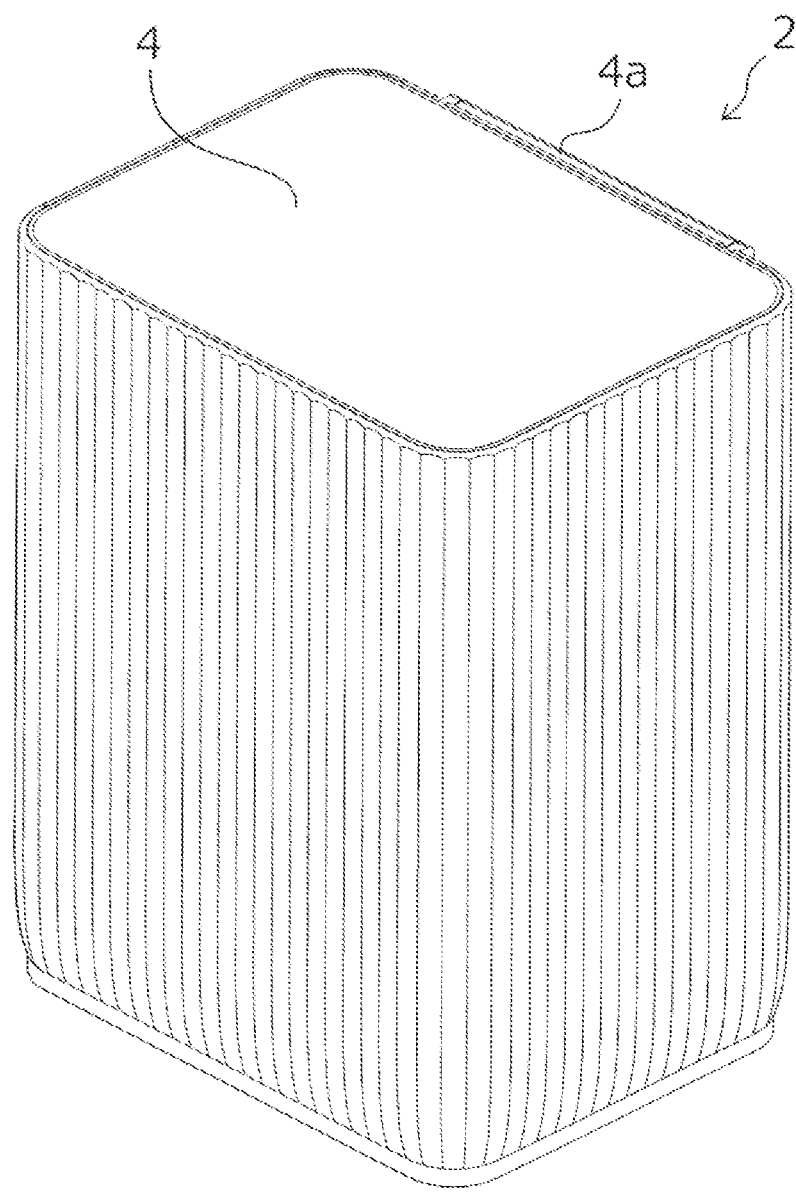
FIG. 2 is a schematic perspective view from the front side of a liquid supply device in the liquid ejection device of FIG. 1 and illustrates a state in which a lid is closed.
Figure 3:
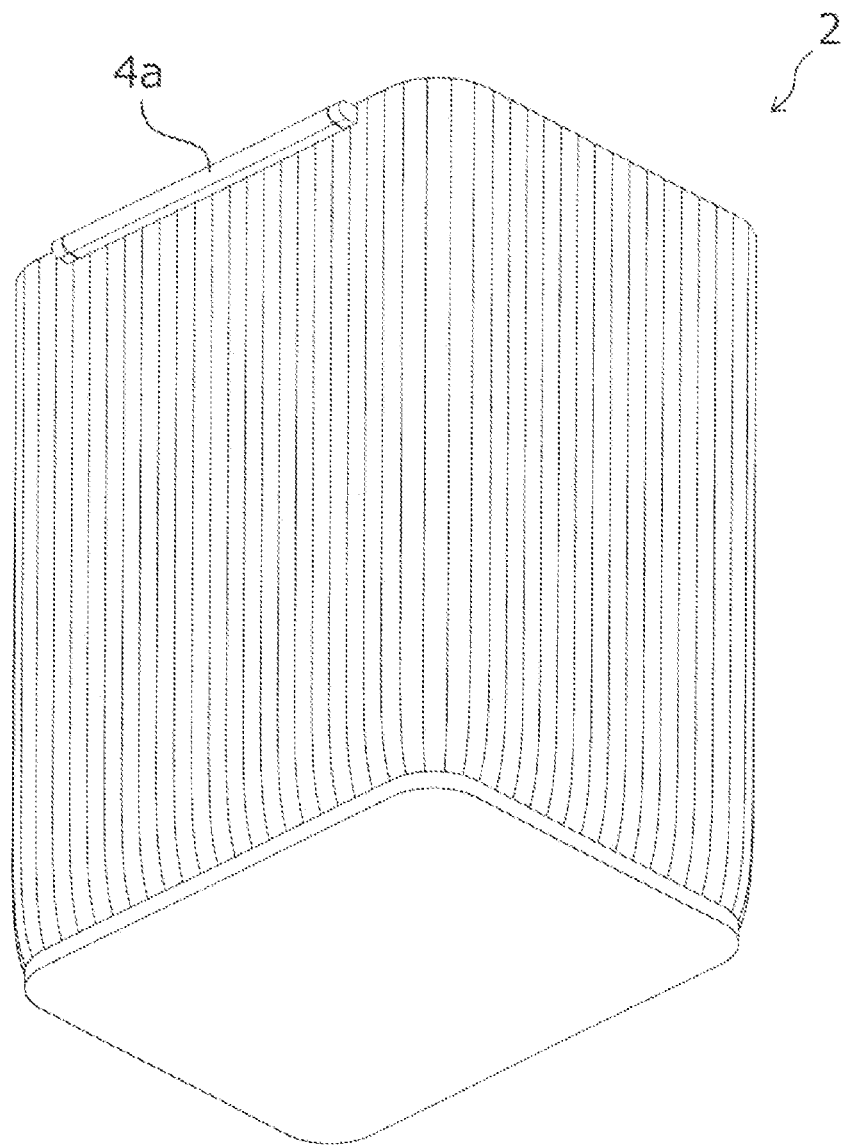
FIG. 3 is a schematic perspective view from the back side of the liquid supply device in the liquid ejection device of FIG. 1.

As illustrated in FIG. 1, the liquid supply device 2 includes a lid part 4, an operating part 5, a liquid accommodating part 6 configured to store a liquid to be ejected, and a liquid supply path 10 that connects the liquid accommodating part 6 to the liquid ejection nozzle 3. The lid part 4 can be displaced in an open state as illustrated in FIG. 1 and a closed state as illustrated in FIGS. 2 and 3 by rotating around a rotating shaft part 4a. A pump (not illustrated) is provided inside the liquid supply device 2, and a liquid can be supplied from the liquid accommodating part 6 to the liquid ejection nozzle 3 via the liquid supply path 10 by a pressure of the pump.

Figure 4:
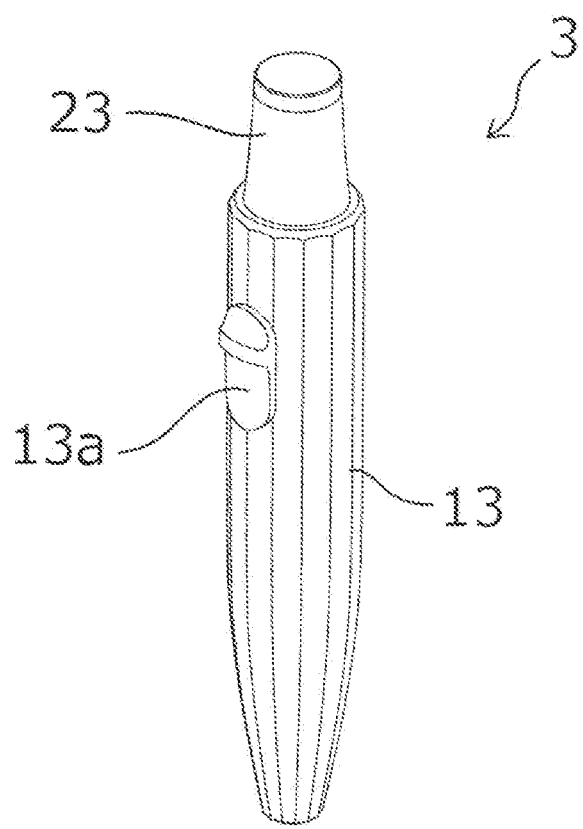
FIG. 4 is a schematic perspective view of a liquid ejection nozzle in the liquid ejection device of FIG. 1.
Figure 5:
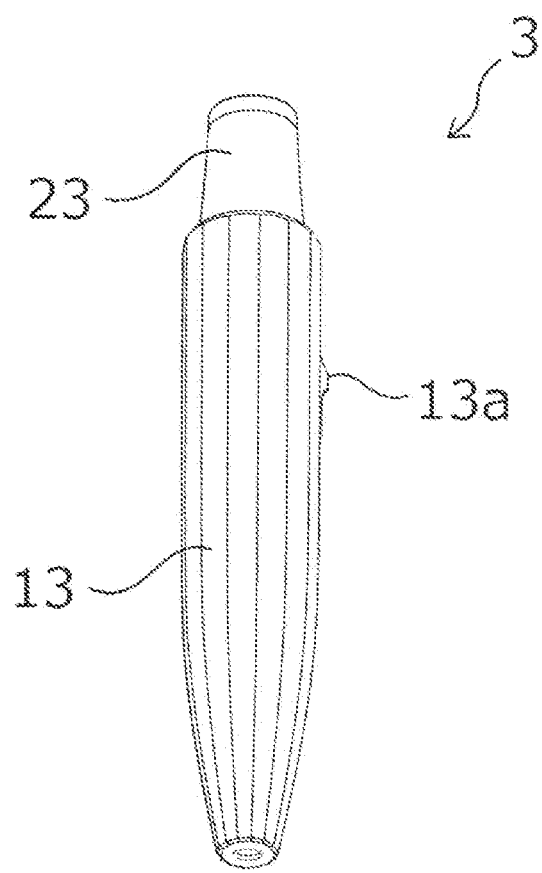
FIG. 5 is a schematic perspective view of the liquid ejection nozzle of the liquid ejection device of FIG. 1 when seen in a direction different from that of FIG. 4.

As illustrated in FIGS. 1, 4, and 5, the liquid ejection nozzle 3 includes a handpiece unit 13 and a nozzle unit 23. A switch 13a is provided at the handpiece unit 13, a liquid is ejected from the nozzle unit 23 by a user turning on the switch 13a, and ejection of the liquid from the nozzle unit 23 stops when the user turns off the switch 13a.

Figure 6:
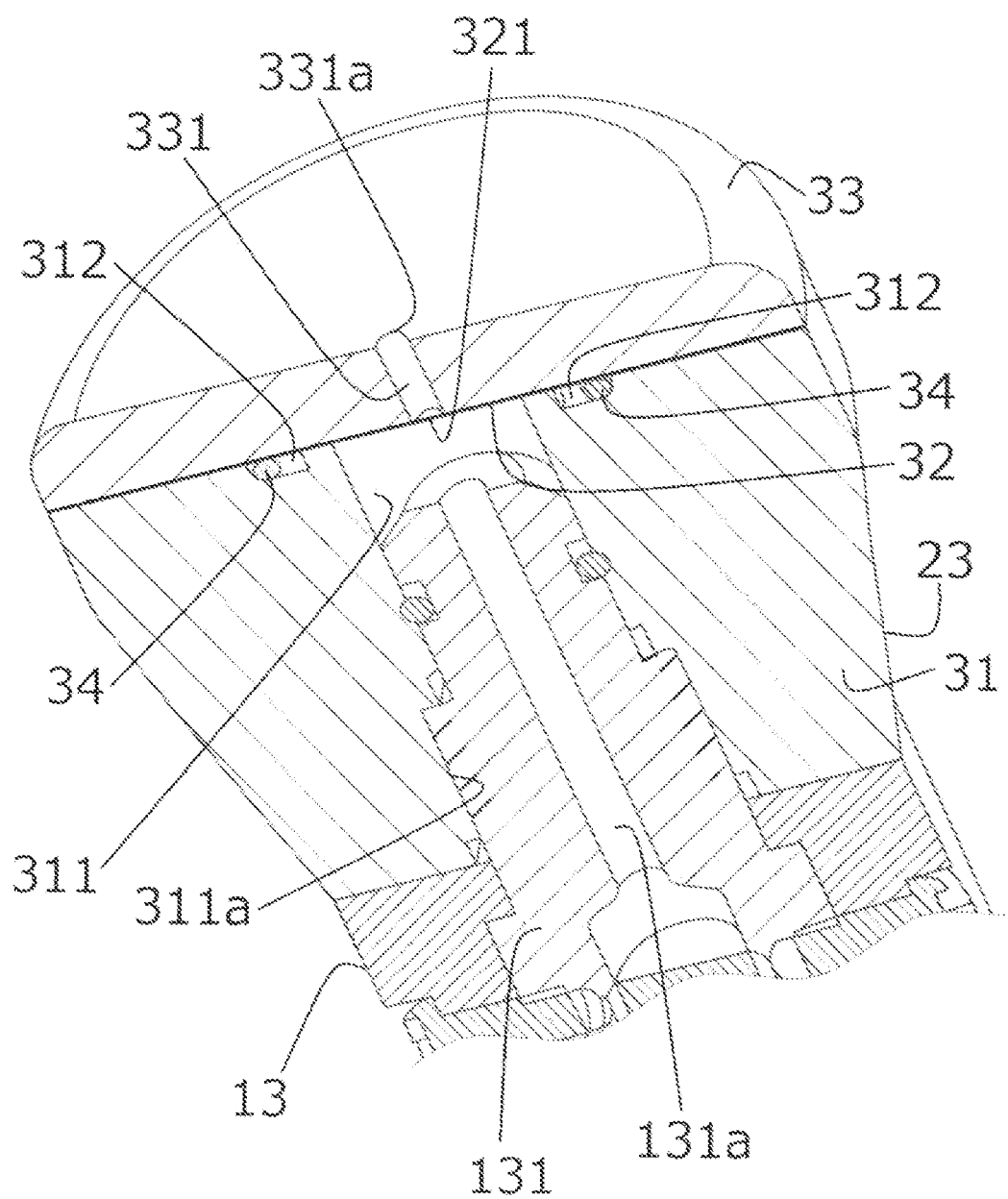
FIG. 6 is a perspective cross-sectional view of a tip end portion of the liquid ejection nozzle in the liquid ejection device of FIG. 1.
Figure 7:
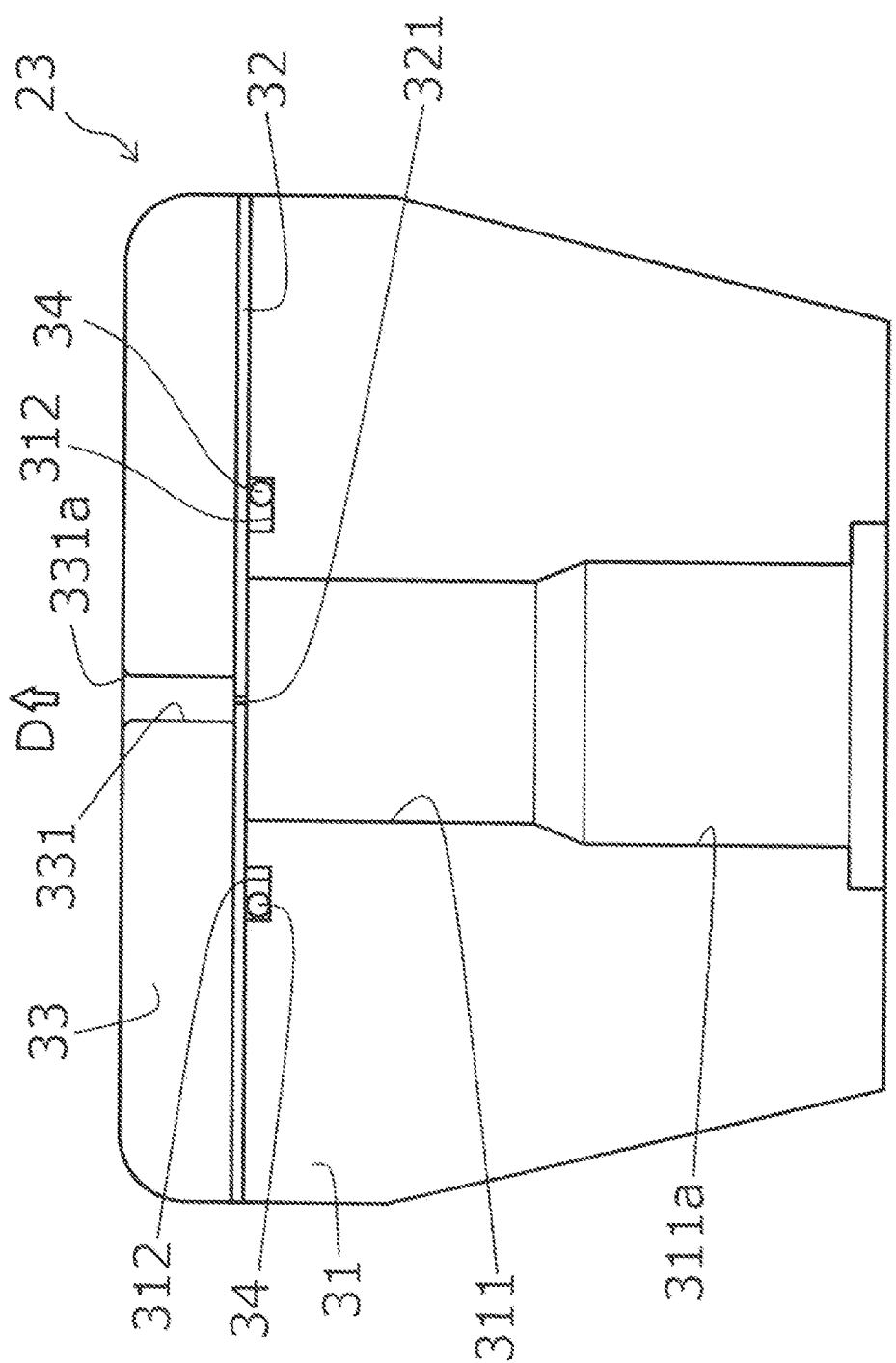
FIG. 7 is a cross-sectional view of a nozzle unit of the liquid ejection nozzle of FIG. 6.

Next, details of the nozzle unit 23 of the liquid ejection device 1 of the embodiment will be described in detail with reference to FIGS. 6 to 9. As illustrated in FIG. 6, the nozzle unit 23 is installed at a tip end of the handpiece unit 13. Specifically, as illustrated in FIG. 6, a male thread part 131 in which a liquid flow path 131a is formed is provided on the tip end of the handpiece unit 13. Then, as illustrated in FIGS. 6 and 7, a male thread mounting part 311 provided with a female thread part 311a is formed inside a base part 31 of the nozzle unit 23, and the nozzle unit 23 is mounted on the tip end of the handpiece unit 13 by fitting the male thread part 131 to the female thread part 311a. Here, "tip end" refers to a tip end in an ejection direction D of the liquid illustrated in FIG. 7. Although the nozzle unit 23 is mounted on the handpiece unit 13 by fitting the male thread part 131 to the female thread part 311a in the embodiment, the present disclosure is not limited to such a configuration, and for example, a protrusion and a recess may be respectively provided at the nozzle unit 23 and the handpiece unit 13, and a snap fit method in which the protrusion is mated with the recess may be used. A nozzle hole 321 and a through hole 331 are minute things that cannot be visually recognized by the naked eye and thus are not illustrated in FIG. 4.

Figure 8:
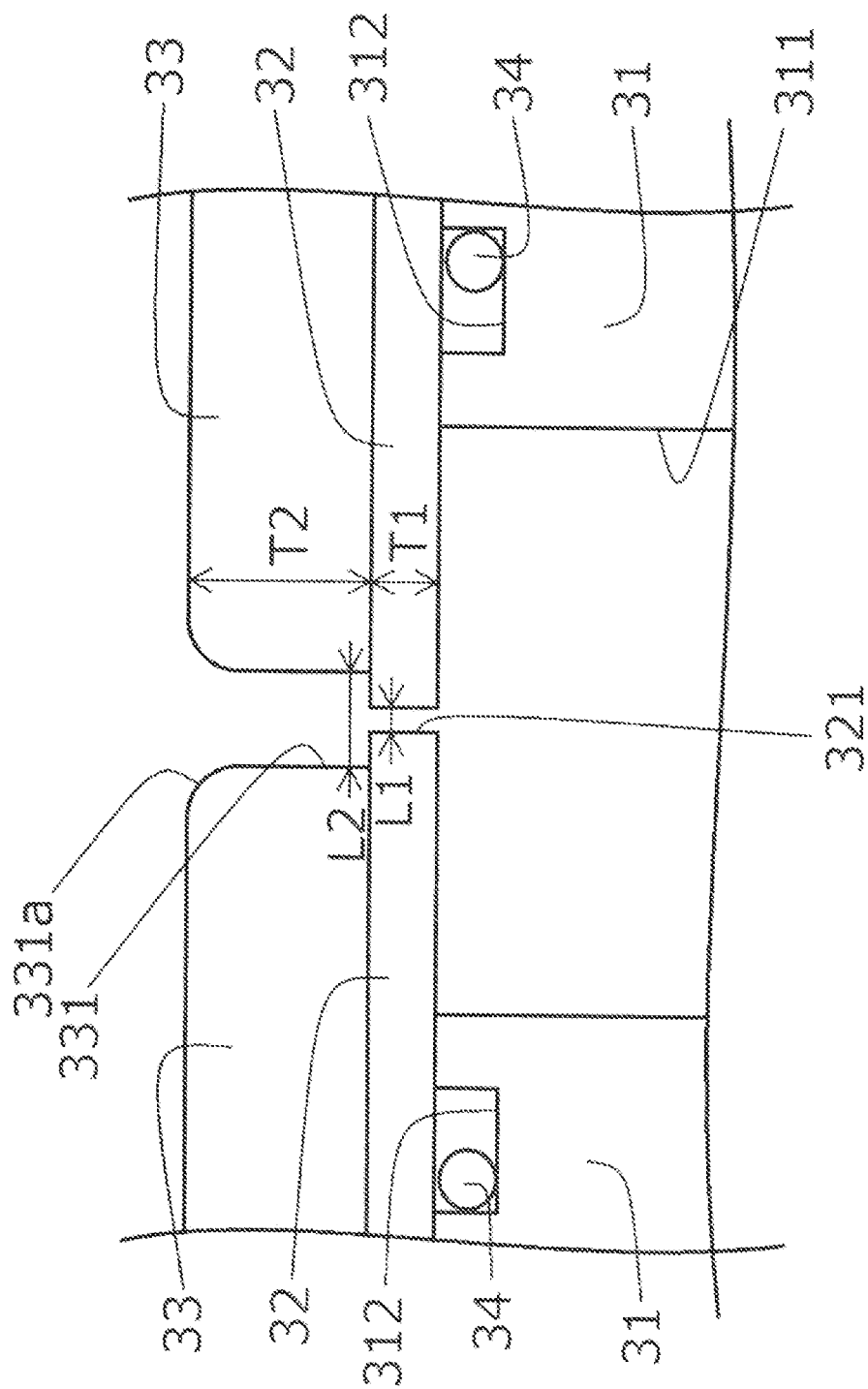
FIG. 8 is an enlarged view of a periphery of a nozzle plate of the nozzle unit of FIG. 7.

As illustrated in FIGS. 7 and 8, a nozzle plate 32 is fixed to the tip end side of the base part 31. A method of fixing the nozzle plate 32 to the base part 31 is not particularly limited. The nozzle hole 321 is provided in the nozzle plate 32. Additionally, a groove 312 is formed in the base part 31 to have an annular shape when seen in the ejection direction D, and an O-ring 34 is disposed as a sealing member in the groove 312. With such a configuration, the liquid does not leak to the outside of the O-ring 34 via a gap between the base part 31 and the nozzle plate 32 in a direction intersecting the ejection direction D. The embodiment has the configuration in which the O-ring 34 is used to eliminate use of an adhesive and to avoid elution of the adhesive, but the present disclosure is not limited to such a configuration. Furthermore, as a material of the O-ring 34, fluorine rubber, silicon rubber, or EPDM can be used to avoid elution from the O-ring 34.

Further, as illustrated in FIGS. 7 and 8, a pressing member 33 is fixed to the tip end side of the nozzle plate 32. In the embodiment, the pressing member 33 is fixed to the tip end side of the nozzle plate 32 by the pressing member 33 being engaged with the base part 31 by an engagement portion (not illustrated), but the method of fixing the pressing member 33 to the base part 31 or the nozzle plate 32 is not particularly limited. As illustrated in FIGS. 6 to 9, the through hole 331 is formed at a position corresponding to the nozzle hole 321 in the pressing member 33, that is, at a position on an extension line downstream of the nozzle hole 321 in the ejection direction D. Because the liquid ejection nozzle 3 has such a configuration, the liquid supplied from the liquid supply device 2 to the liquid ejection nozzle 3 is ejected in the ejection direction D of FIG. 7 via a liquid flow path inside the handpiece unit 13, the liquid flow path 131a, a space portion of the male thread mounting part 311, the nozzle hole 321, and the through hole 331.

As illustrated in FIG. 8, a diameter L2 of the through hole 331 is sufficiently larger than a diameter L1 of the nozzle hole 321, and the liquid ejected from the nozzle hole 321 does not come into contact with the through hole 331. In addition, as illustrated in FIG. 8, a thickness T2 of the pressing member 33 in the ejection direction D is sufficiently greater than a thickness T1 of the nozzle plate 32, and the pressing member 33 is highly rigid. Here, the expression "the thickness T2 of the pressing member 33 is sufficiently larger than the thickness T1 of the nozzle plate 32" means that the thickness T2 of the pressing member 33 can be 10 times the thickness T1 of the nozzle plate 32 or greater, for example. Thus, when the liquid is ejected from the nozzle hole 321, a force is applied to the nozzle plate 32 in the ejection direction D, but the pressing member 33 can firmly press down on the nozzle plate 32.

As described above, the liquid ejection nozzle 3 of the embodiment is a liquid ejection nozzle that has the nozzle hole 321 and ejects a liquid from the nozzle hole 321 in the ejection direction D toward the skin or the like as a target subject. Additionally, the liquid ejection nozzle 3 of the embodiment includes the nozzle plate 32 having the nozzle hole 321, and the pressing member 33 that has the through hole 331 with a diameter greater than the diameter of the nozzle hole 321 at a position corresponding to the nozzle hole 321 in the ejection direction D and presses down the nozzle plate 32 from the downstream side in the ejection direction D.

As described above, the liquid ejection nozzle 3 of the embodiment includes the pressing member 33 that presses down the nozzle plate 32 from the downstream side in the ejection direction D. As a result, deformation of the nozzle plate 32 due to a pressure applied to the nozzle plate 32 can be suppressed. In addition, the diameter L2 of the through hole 331 of the pressing member 33 is larger than the diameter L1 of the nozzle hole 321. Thus, when the liquid is ejected from the nozzle hole 321, the liquid ejection nozzle 3 of the embodiment can suppress interference of the pressing member 33 in the ejection of the liquid from the nozzle hole 321.

Figure 9:
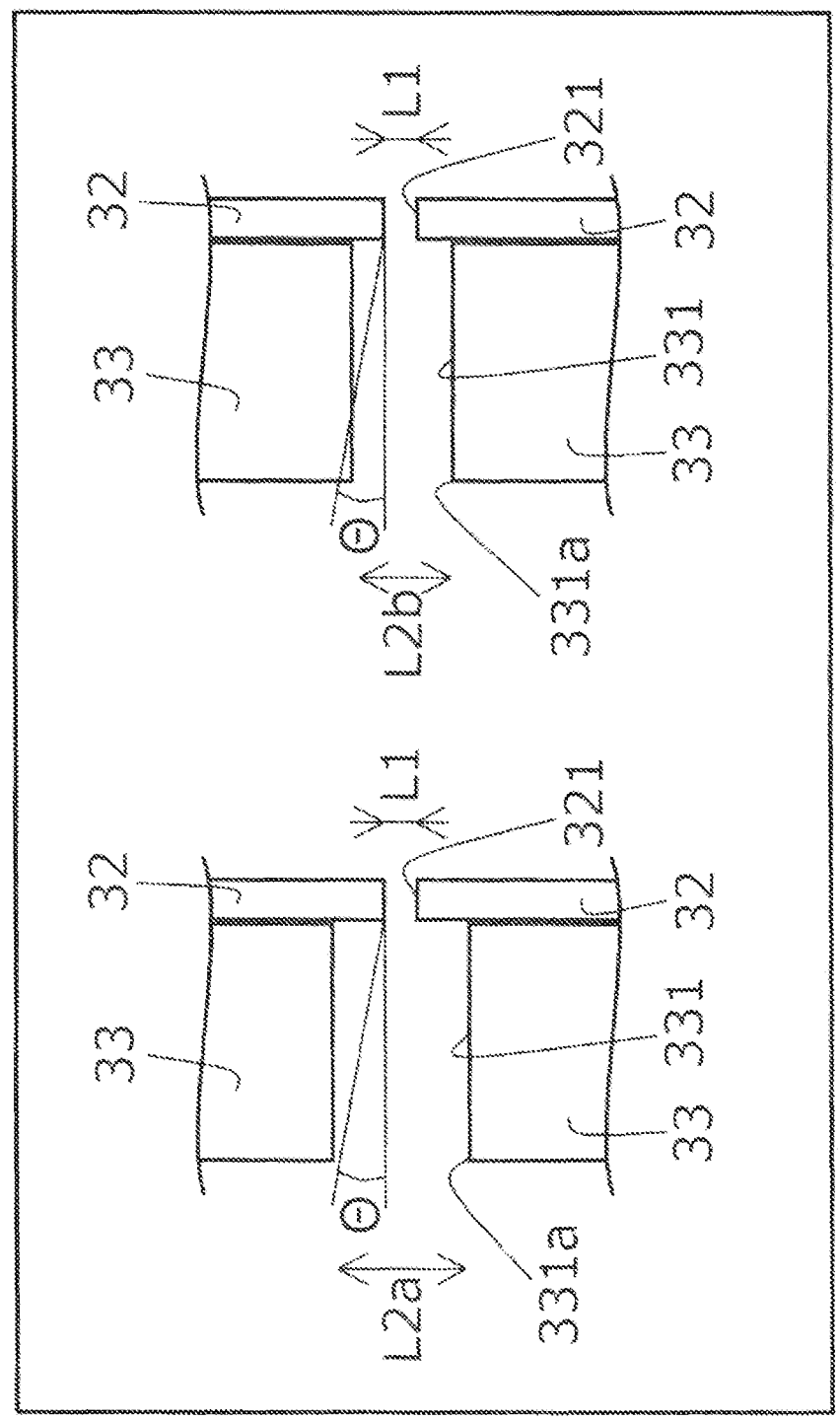
FIG. 9 is a schematic view for describing an arrangement relationship between a nozzle hole of the nozzle plate and a through hole of a pressing member.

Here, a preferred range of the diameter L2 of the through hole 331 will be described with reference to FIG. 9. The left side of the drawing of FIG. 9 illustrates an example of a case in which the diameter L2 of the through hole 331 has a diameter L2a that is within a preferred range, and the right side of FIG. 9 illustrates an example of a case in which the diameter L2 of the through hole 331 has a diameter L2b that is not within a preferable range. The diameter L1 of the nozzle hole 321 corresponds to a diameter of the liquid to be ejected and thus can be appropriately set according to uses or the like.

In FIG. 9, the maximum deviation of the ejection direction from a predetermined ejection direction D in the liquid ejection nozzle 3 of the embodiment is referred to as an inclination angle θ. The inclination angle θ is preferably 0°, but may be, for example, about 2° due to manufacturing tolerance or the like. In the left drawing of FIG. 9, the diameter L2 of the through hole 331 is the diameter L2a. The diameter L2a has a size in which the liquid ejected from the nozzle hole 321 does not come into contact with the through hole 331 even when the liquid is ejected at the inclination angle θ at which the maximum deviation of the ejection direction occurs. Thus, in a case in which the diameter L2 is applied as in the left drawing of FIG. 9, even when the liquid ejected from the nozzle hole 321 is ejected at the inclination angle θ at which the maximum deviation of the ejection direction occurs, the liquid is ejected without interfering with the through hole 331. A relation in which the liquid does not come into contact with the through hole 331 can be expressed using the inclination angle θ, the diameter L1 of the nozzle hole 321, the diameter L2 of the through hole 331, and the thickness T2 of the pressing member 33 as shown in the following Equation 1:

$$\theta < \tan^{-1}(((L2-L1)/2)/T2). \quad \text{(Equation 1)}:$$

On the other hand, in the right drawing of FIG. 9, the diameter L2 of the through hole 331 is a diameter L2b. The diameter L2b has a size in which the liquid ejected from the nozzle hole 321 comes into contact with a tip end portion 331a of the through hole 331 when the liquid is ejected at the inclination angle θ at which the maximum deviation of the ejection direction occurs. In a case in which the diameter L2 as illustrated in the right drawing of FIG. 9 is formed, when the liquid ejected from the nozzle hole 321 is ejected at the inclination angle θ at which the maximum deviation of the ejection direction occurs, the liquid is ejected while being interfered with by the through hole 331. When the liquid is ejected while being interfered with by the through hole 331, it may cause an ejection failure, the through hole 331 may be wetted, and thus foreign matter may easily adhere to the through hole 331.

Therefore, the diameter L2 of the through hole 331 preferably has a size in which the liquid ejected from the nozzle hole 321 does not come into contact with the through hole 331 even when the liquid ejected from the nozzle hole 321 is ejected at the inclination angle θ at which the maximum deviation of the ejection direction occurs. The size that does not come into contact with the through hole 331 varies in accordance with the thickness T2 of the pressing member 33, and thus a lower limit value of the diameter L2 of the through hole 331 also varies in accordance with the thickness T2 of the pressing member 33.

In addition, a preferred upper limit value of the diameter L2 of the through hole 331 is equal to or less than the thickness T2 of the pressing member 33 in the ejection direction D. When the diameter of the through hole 331 is too large or the thickness T2 of the pressing member 33 is too small, the effect of suppressing the nozzle plate 32 of the pressing member 33 is reduced. However, a reduction in the effect of suppressing the nozzle plate 32 of the pressing member 33 can be suppressed by setting the diameter L2 of the through hole 331 to be equal to or less than the thickness T2 of the pressing member 33 in the ejection direction D.

In the embodiment, the inclination angle θ that is the deviation from the predetermined ejection direction D is allowed to be 2°. In this way, it is particularly preferable to set the inclination angle θ to 2° or less. The allowable inclination angle θ is preferably at least equal to or less than 45°, and thus the diameter of the through hole is preferably a diameter in which the liquid does not come into contact with the through hole 331 even when the inclination angle θ deviates from the predetermined ejection direction D by 45°. The upper limit of the diameter L2 of the through hole 331 when the allowable inclination angle is 45° and the diameter of the through hole 331 does not come into contact with the liquid has the same length as the thickness T2 of the pressing member 33.

Here, the pressing member 33 is configured to be attached to and detached from the nozzle plate 32. As a result, the pressing member can be easily replaced or cleaned. In the embodiment, the liquid ejection device 1 can be used even when the pressing member 33 is removed from the nozzle plate 32. However, the present disclosure is not limited to the above described configuration. For example, the pressing member 33 and the nozzle plate may be integrally formed by, for example, insert molding.

Furthermore, in the liquid ejection nozzle 3 of the embodiment, the entire pressing member 33 is constituted of a resin. In this way, the pressing member 33 is preferably configured to include a resin. This is because a resin can easily change a shape, and thus the pressing member 33 having the through hole 331 can be easily manufactured using a resin. In addition, a resin has an advantage that it does not easily corrode.

Additionally, in the liquid ejection nozzle 3 of the embodiment, the through hole 331 of the pressing member 33 is subjected to a liquid repellent treatment against the liquid. As a result, when the liquid is ejected, the liquid wet-spreads at the through hole 331 and is subjected to a force from the through hole 331, and thus it is possible to suppress a decrease in ejection accuracy. A liquid repellent treatment method is not particularly limited, and examples thereof include applying a fluorine compound to the through hole 331.

In addition, as illustrated in FIG. 8, in the pressing member 33 of the liquid ejection nozzle 3 of the embodiment, the tip end portion 331a of the through hole 331 is chamfered. Because the tip end portion 331a of the through hole 331 is chamfered in this way, when the user uses the liquid ejection device 1 of the embodiment, sebum and the like are less likely to adhere to the through hole 331. However, the present disclosure is not limited to the above described configuration.

Second Embodiment

Figure 10:
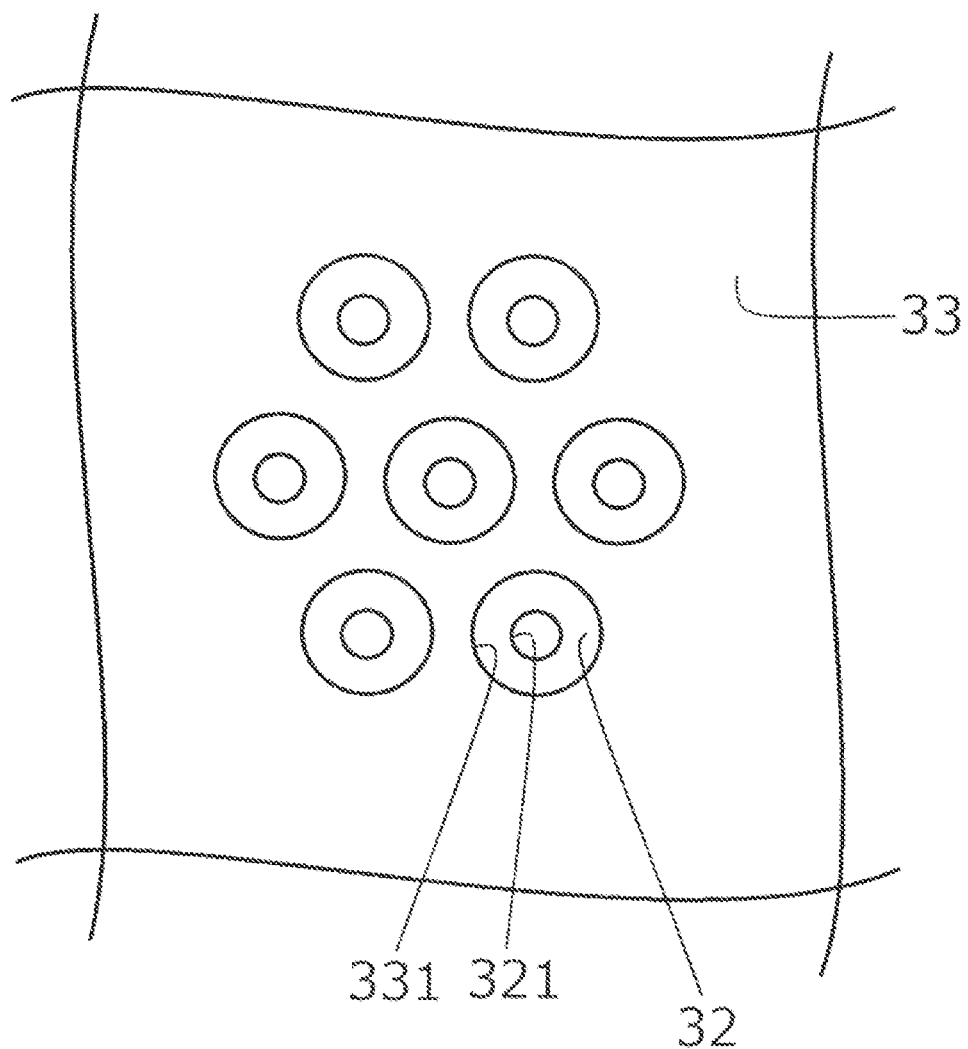
FIG. 10 is a view of a nozzle hole of a nozzle plate and a through hole of a pressing member in a liquid ejection nozzle according to a second embodiment of the present disclosure when seen in an ejection direction.
Figure 11:
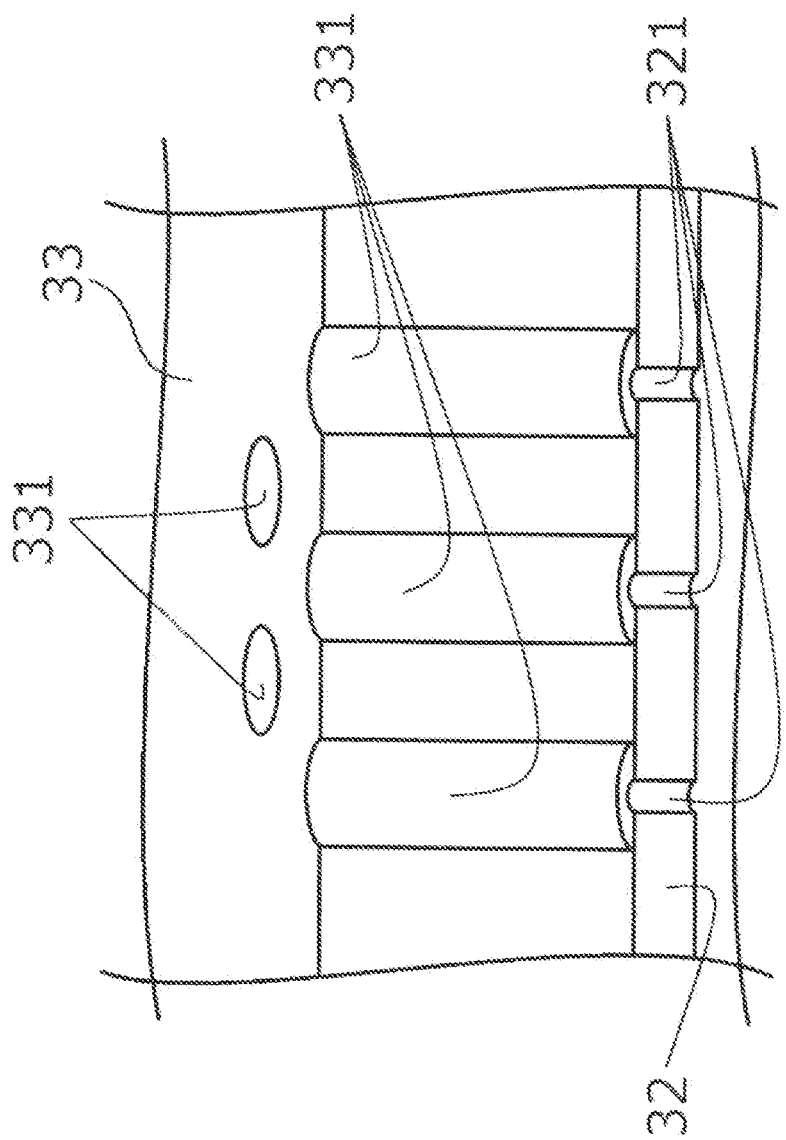
FIG. 11 is a cross-sectional view illustrating the nozzle hole of the nozzle plate and the through hole of the pressing member in the liquid ejection nozzle according to the second embodiment of the present disclosure.

Next, a liquid ejection device 1 of a second embodiment will be described with reference to FIGS. 10 and 11. In FIGS. 10 and 11, the constituent members common to those in the first embodiment described above are designated by the same reference numerals, and detailed description thereof will be omitted. Here, the liquid ejection device 1 of the embodiment has the same characteristics as those in the liquid ejection device 1 of the first embodiment described above and is configured in the same manner as the liquid ejection device 1 of the first embodiment except for the following description. Specifically, the same configuration as that in the liquid ejection device 1 of the first embodiment is used except for having a plurality of nozzle holes 321 and through holes 331.

As illustrated in FIGS. 10 and 11, in the liquid ejection nozzle 3 of the liquid ejection device 1 of the embodiment, a plurality of nozzle holes 321 are provided in the nozzle plate 32. As a result, the diameter of one nozzle hole 321 can be reduced without decreasing the ejection amount of the liquid, and a sufficient amount of the liquid can be ejected at high speed. This is because, when the liquid is ejected at the same pressure, the liquid can be ejected at a higher speed by reducing the diameter of the nozzle hole 321.

As illustrated in FIGS. 10 and 11, in the liquid ejection nozzle 3 of the liquid ejection device 1 of the embodiment, one through hole 331 is provided corresponding to each of nozzle holes 321. When the diameter L2 of the through hole 331 is too large, the effect of suppressing the nozzle plate by the pressing member 33 may decrease. However, as described above, in the liquid ejection nozzle 3 of the embodiment, one through hole 331 is provided corresponding to each of the nozzle holes 321. As a result, it is possible to suppress excessive enlargement of one through hole 331, and thus the decrease in the effect of suppressing the nozzle plate 32 of the pressing member 33 is suppressed.

Third Embodiment

Figure 12:
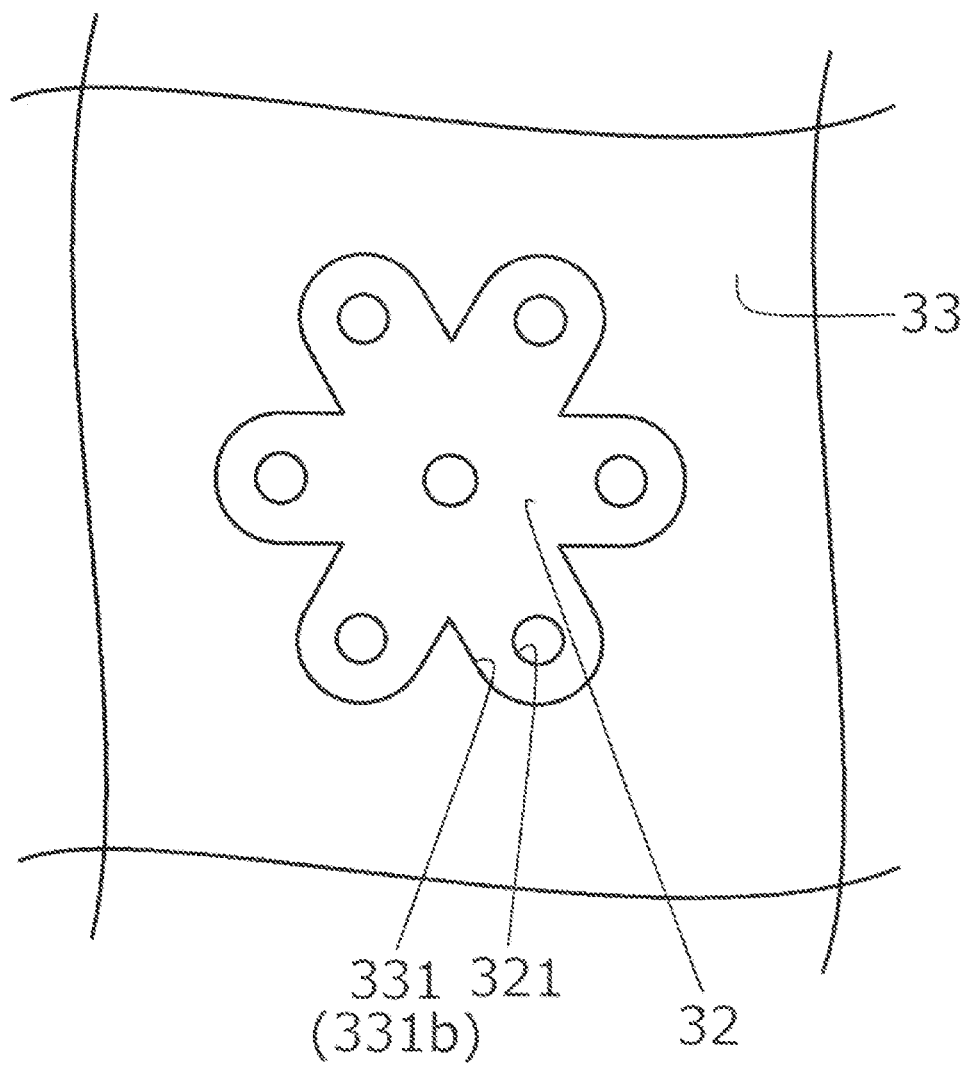
FIG. 12 is a view of a nozzle hole of a nozzle plate and a through hole of a pressing member in a liquid ejection nozzle according to a third embodiment of the present disclosure when seen in an ejection direction.
Figure 13:
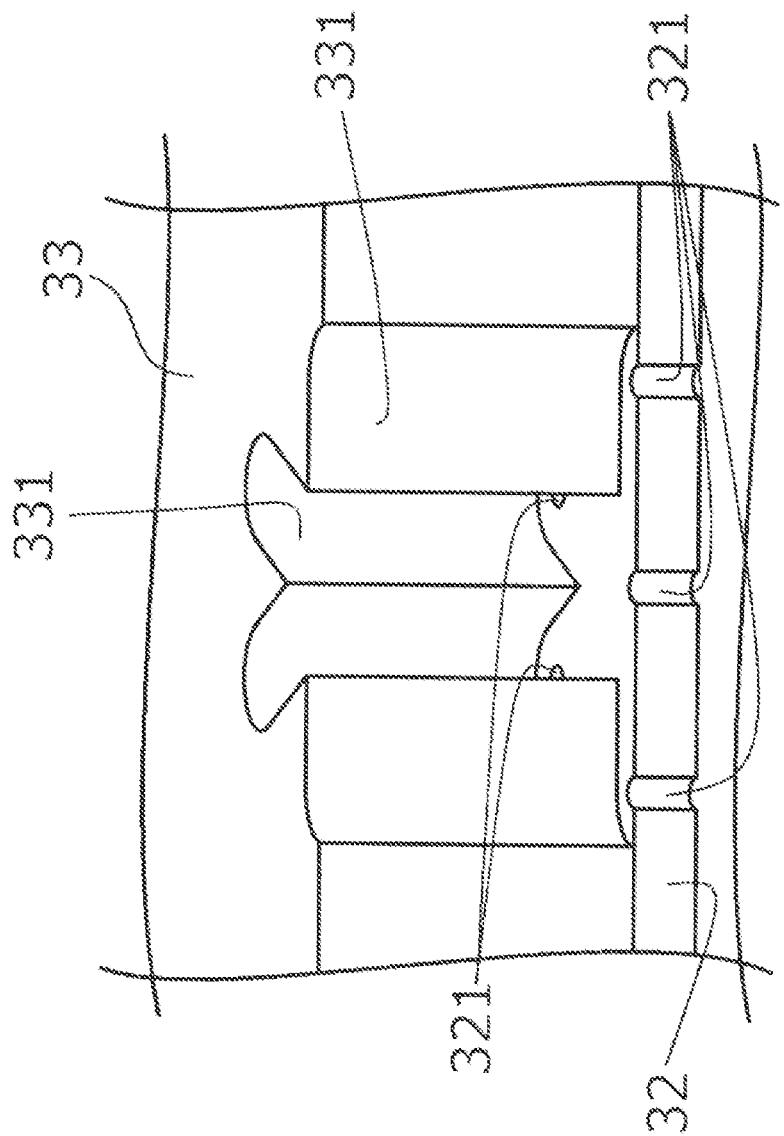
FIG. 13 is a cross-sectional view illustrating the nozzle hole of the nozzle plate and the through hole of the pressing member in the liquid ejection nozzle according to the third embodiment of the present disclosure.

Next, a liquid ejection device 1 of a third embodiment will be described with reference to FIGS. 12 and 13. FIGS. 12 and 13 are views corresponding to FIGS. 10 and 11 of the liquid ejection device 1 of the second embodiment. Further, in FIGS. 12 and 13, the constituent members common to those of the first and second embodiments are designated by the same reference numerals, and detailed description thereof will be omitted. Here, the liquid ejection device 1 of the embodiment has the same characteristics as those in the liquid ejection device 1 of the first and second embodiments described above, and is configured in the same manner as the liquid ejection device 1 of the first and second embodiments except for the following description. Specifically, it has the same configuration as the liquid ejection device 1 of the first embodiment except that it has a specific shape of the through hole 331 and a plurality of nozzle holes 321.

As illustrated in FIGS. 12 and 13, in the liquid ejection nozzle 3 of the embodiment, a plurality of nozzle holes 321 are also provided in the nozzle plate 32 as in the liquid ejection nozzle 3 of the second embodiment. As a result, the diameter of one nozzle hole 321 can be reduced without decreasing the ejection amount of the liquid, and a sufficient amount of the liquid can be ejected at high speed.

On the other hand, as illustrated in FIGS. 12 and 13, in the liquid ejection nozzle 3 of the embodiment, one through hole 331 is provided corresponding to the plurality of nozzle holes 321. In this way, the pressing member 33 having the through hole 331 is easily manufactured by reducing the number of through holes 331. Further, an interval between the nozzle holes 321 can be made narrower.

As illustrated in FIG. 12, the through hole 331 of the embodiment has a configuration in which a wall 331b protrudes toward the center so that an opening area decreases as much as possible while a predetermined interval with respect to the nozzle holes 321 is ensured when seen in the ejection direction D. With such a configuration, excessive enlargement of the through hole 331 is suppressed, and the decrease in the effect of suppressing the nozzle plate 32 of the pressing member 33 is suppressed. However, the present disclosure is not limited to such a configuration, and for example, the through hole 331 may be configured so that the wall 331b is circular when seen in the ejection direction D.

In the case of a configuration such as that of the embodiment, the liquids ejected from the adjacent nozzle holes 321 preferably do not interfere with each other even when the liquids are deviated from the predetermined ejection direction D. As described above, the liquid may be ejected while deviating from the predetermined ejection direction D due to manufacturing tolerances and the like, as described above, the interval between the adjacent nozzle holes 321 that can suppress interference between the liquids ejected from adjacent nozzle holes 321 changes in accordance with the thickness T2 of the pressing member 33. For example, when the thickness T2 of the pressing member 33 is 10 mm, in a case in which the inclination angle θ from the predetermined ejection direction D is 1.4° or greater, the interval between the adjacent nozzle holes 321 is preferably 0.25 mm or more.

On the other hand, when the thickness T2 of the pressing member 33 is 10 mm, in a case in which the interval between the adjacent nozzle holes 321 is 0.25 mm, the inclination angle θ from the predetermined ejection direction D is preferably suppressed to 1.4° or less. Similarly, when the thickness T2 of the pressing member 33 is 10 mm, in a case in which the interval between the adjacent nozzle holes 321 is 0.5 mm, the inclination angle θ from the predetermined ejection direction D is preferably suppressed to 2.9° or less, in a case in which the interval between the adjacent nozzle holes 321 is 1.0 mm, the inclination angle θ from the predetermined ejection direction D is preferably suppressed to 3.8° or less, and in a case in which the interval between the adjacent nozzle holes 321 is 1.5 mm, the inclination angle θ from the predetermined ejection direction D is preferably suppressed to 5.7° or less.

Fourth Embodiment

Figure 14:
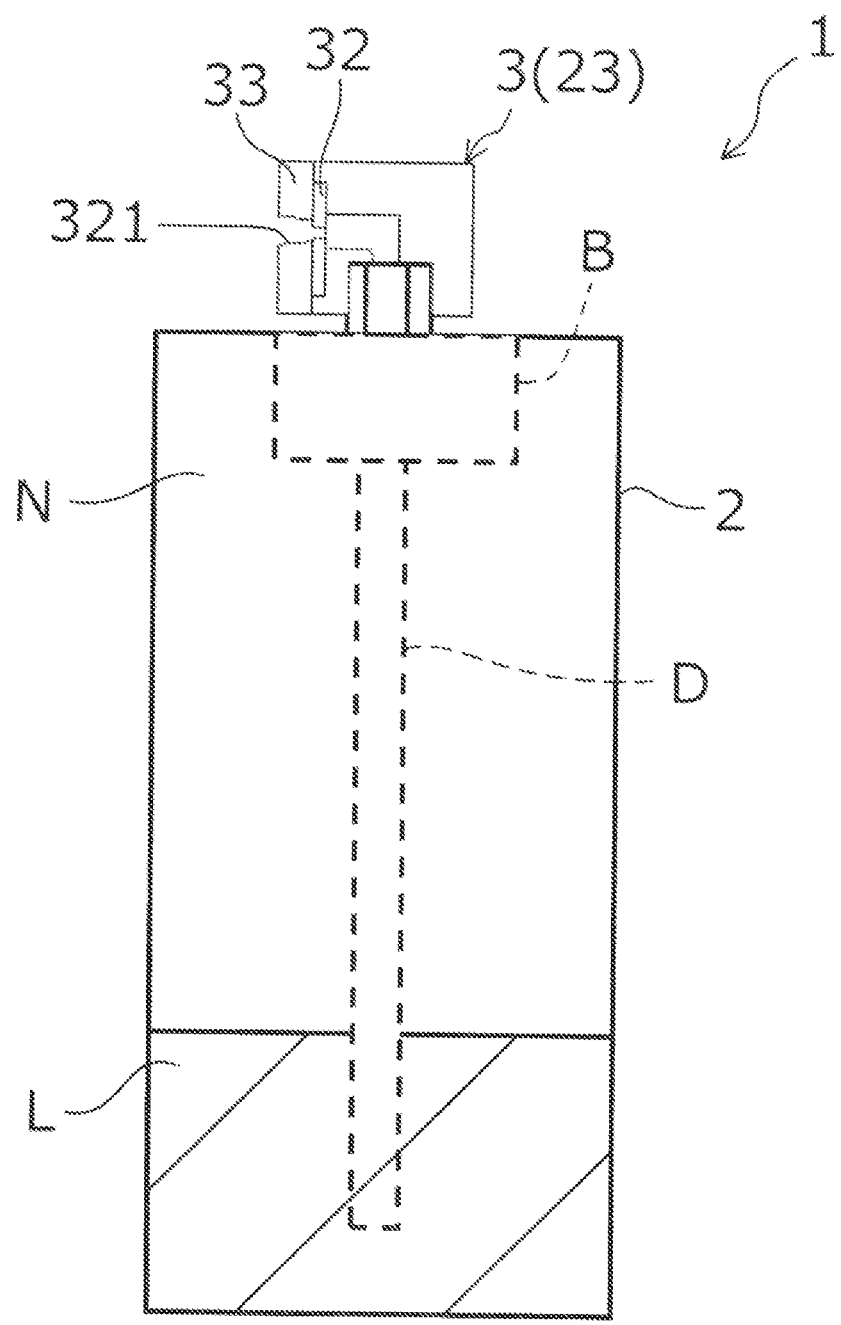
FIG. 14 is a schematic cross-sectional view of an entire liquid ejection device having a liquid ejection nozzle according to a fourth embodiment of the present disclosure.
Figure 15:
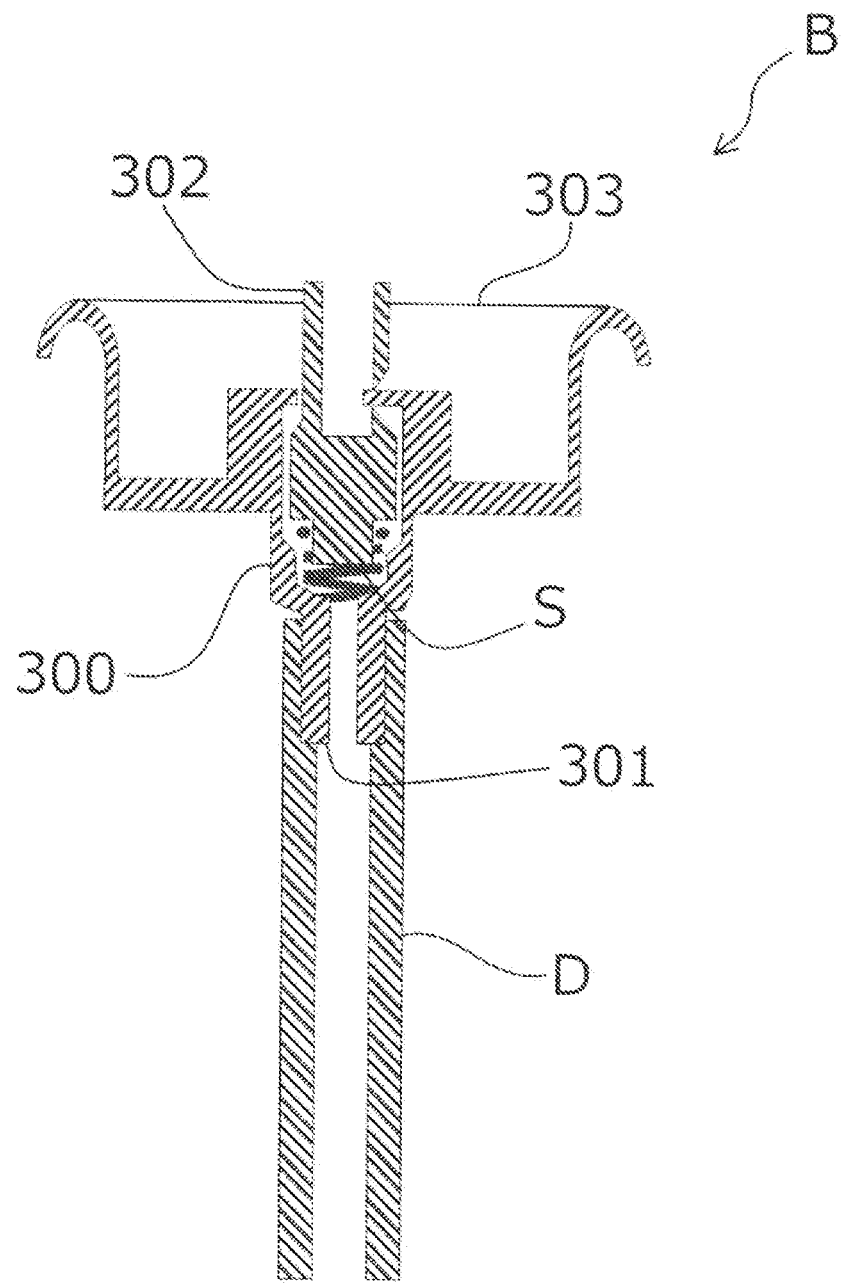
FIG. 15 is a cross-sectional view of a valve applicable to the liquid ejection nozzle according to the fourth embodiment of the present disclosure.

Next, a liquid ejection device 1 of a fourth embodiment will be described with reference to FIGS. 14 and 15. In FIGS. 14 and 15, the constituent members common to those in the first to third embodiments are designated by the same reference numerals, and detailed description thereof will be omitted. Here, the liquid ejection device 1 of the embodiment has a configuration in which the liquid enclosed inside a container is fed by a gas pressure.

As illustrated in FIG. 14, the liquid supply device 2 of the embodiment is an aerosol can, and a nitrogen gas N compressed to high pressure and a liquid L are enclosed in the liquid supply device 2. The liquid L is supplied to the liquid ejection nozzle 3, which is an actuator, via a liquid supply path D and a valve B, due to a pressure of the nitrogen gas N inside the liquid supply device 2. The gas enclosed in the aerosol can is not limited to a compressed gas such as nitrogen or carbon dioxide and may be a liquefied gas such as dimethyl ether or liquefied natural gas.

When the user presses down the liquid ejection nozzle 3 which is an actuator, the valve B opens and the liquid L is ejected from the nozzle hole 321. Furthermore, the valve B blocks a flow path of the liquid L by a user opening the liquid ejection nozzle 3 which is an actuator, and the ejection of the liquid L from the nozzle hole 321 stops.

Here, in the liquid supply device 2 of the embodiment, the nozzle unit 23 is installed at the valve B by press fitting. However, in order to prevent the nozzle unit 23 from being disassembled or modified, the nozzle unit 23 may be adhered to the valve B. In addition, the liquid ejection nozzle 3 of the embodiment has a structure including the nozzle plate 32, and has a structure in which the pressing member 33 can be removed and the nozzle plate 32 can be assembled and replaced. However, the present disclosure is not limited to such a structure, and a structure in which the nozzle plate 32 is integrally molded with the liquid ejection nozzle 3 which is an actuator, a structure in which the nozzle plate 32 and the pressing member 33 are integrally molded with the liquid ejection nozzle 3 which is an actuator, a structure in which a part in which the nozzle plate 32 is unitized is press-fitted or fitted to the actuator, or the like may be adopted.

FIG. 15 is an example of the valve B in the liquid ejection device 1 of FIG. 14. As illustrated in FIG. 15, the valve B of the embodiment includes a housing 300 having a housing hole 301 and a spring S therein. Additionally, a stem 302 that is pressed by a spring S and a stem gasket 303 that presses the stem 302 are provided. When the user presses down the liquid ejection nozzle 3, the stem 302 is moved down, a gap is formed between the stem gasket 303 and the stem 302, and the liquid supply path D opens. In addition, when the user opens the liquid ejection nozzle 3, the stem 302 is pressed upward by the spring S, the gap between the stem gasket 303 and the stem 302 is eliminated, and thus the liquid supply path D is closed.

The present disclosure is not limited to the embodiments described above, and can be realized in various configurations without departing from the gist of the present disclosure. Appropriate replacements or combinations may be made to the technical features in the embodiments which correspond to the technical features in the aspects described in the SUMMARY section to solve some or all of the problems described above or to achieve some or all of the advantageous effects described above. Additionally, when the technical features are not described herein as essential technical features, such technical features may be deleted appropriately.

What is claimed is:

1. A liquid ejection nozzle that has a nozzle hole and ejects a liquid from the nozzle hole in an ejection direction toward a target subject, the liquid ejection nozzle comprising:

a nozzle plate having the nozzle hole; and a pressing member having a through hole having a diameter larger than a diameter of the nozzle hole at a position corresponding to the nozzle hole in the ejection direction, wherein the pressing member is configured to press the nozzle plate from a downstream side in the ejection direction, a surface of the nozzle plate on the ejection direction is in contact with a surface of the pressing member on a side opposite to the ejection direction, a length of the through hole corresponds to a thickness of the pressing member in the ejection direction, and the diameter of the through hole is equal to or less than the thickness of the pressing member.

2. The liquid ejection nozzle according to claim 1, wherein the nozzle plate has a plurality of nozzle holes including the plurality of nozzle hole.

3. The liquid ejection nozzle according to claim 2, wherein the through hole is provided corresponding to each of the plurality of nozzle holes.

4. A liquid ejection device, comprising: the liquid ejection nozzle according to claim 3; and a liquid supply device configured to supply the liquid to the liquid ejection nozzle.

5. The liquid ejection nozzle according to claim 2, wherein the through hole is provided corresponding to the plurality of nozzle holes.

6. A liquid ejection device, comprising: the liquid ejection nozzle according to claim 4; and a liquid supply device configured to supply the liquid to the liquid ejection nozzle.

7. A liquid ejection device, comprising: the liquid ejection nozzle according to claim 2; and a liquid supply device configured to supply the liquid to the liquid ejection nozzle.

8. The liquid ejection nozzle according to claim 1, wherein the pressing member is configured to be attached to and detached from the nozzle plate.

9. A liquid ejection device, comprising: the liquid ejection nozzle according to claim 5; and a liquid supply device configured to supply the liquid to the liquid ejection nozzle.

10. The liquid ejection nozzle according to claim 1, wherein the pressing member includes a resin.

11. A liquid ejection device, comprising: the liquid ejection nozzle according to claim 6; and a liquid supply device configured to supply the liquid to the liquid ejection nozzle.

12. The liquid ejection nozzle according to claim 1, wherein the through hole of the pressing member is subjected to a liquid repellent treatment against the liquid.

13. A liquid ejection device, comprising: the liquid ejection nozzle according to claim 7; and a liquid supply device configured to supply the liquid to the liquid ejection nozzle.

14. A liquid ejection device, comprising: the liquid ejection nozzle according to claim 1; and a liquid supply device configured to supply the liquid to the liquid ejection nozzle.

15. The liquid ejection device according to claim 14, wherein the liquid supply device is configured to feed the liquid to the liquid ejection nozzle using a gas pressure.

16. The liquid ejection nozzle according to claim 1, wherein
a relation in which the liquid does not come into contact with the through hole of the pressing member is expressed by Equation 1:

$$\theta < \tan^{-1}(((L2-L1)/2)/T2) \quad \text{Equation 1, where}$$

θ is an inclination angle representing a maximum deviation of the ejection direction from a specific ejection direction in the liquid ejection nozzle,
L1 is the diameter of the nozzle hole,
L2 is the diameter of the through hole, and
T2 is the thickness of the pressing member in the ejection direction.

17. The liquid ejection nozzle according to claim 16, wherein a tip end portion of the through hole is chamfered.

* * * * *